United States Patent [19]

Bose

[11] 4,260,743
[45] Apr. 7, 1981

[54] PREPARATION OF β-LACTAMS AND INTERMEDIATES THEREFOR

[75] Inventor: Ajay K. Bose, Mountain Lakes, N.J.

[73] Assignee: Gist-Brocades N.V., Delft, Netherlands

[21] Appl. No.: 108,669

[22] Filed: Dec. 31, 1979

Related U.S. Application Data

[63] Continuation-in-part of Ser. No. 969,207, Dec. 13, 1978, abandoned.

[51] Int. Cl.³ .................................... C07D 487/04
[52] U.S. Cl. ........................... 542/442; 260/239 A; 260/347.3; 546/275
[58] Field of Search .................. 260/239 AL, 347.3; 542/455, 442

[56] References Cited

U.S. PATENT DOCUMENTS

| | | | |
|---|---|---|---|
| 3,546,211 | 12/1970 | Bose | 260/239 AL |
| 3,943,123 | 3/1976 | Bose | 260/239 AL |
| 4,207,234 | 6/1980 | Kamiya et al. | 260/347.3 |

OTHER PUBLICATIONS

Sharma et al. I Tetrahedron Letters, No. 14, pp. 1265-1266 (1979).
Sharma et al. II Tetrahedron Letters, No. 46, pp. 4587-4590 (1978).

*Primary Examiner*—John D. Randolph
*Assistant Examiner*—Robert T. Bond
*Attorney, Agent, or Firm*—Hammond & Littell, Weissenberger and Muserlian

[57] ABSTRACT

Novel process for the preparation of β-lactams of the formulae:

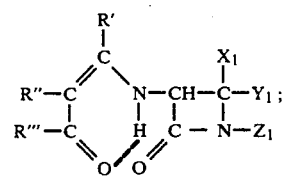

IV A

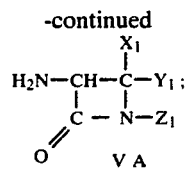

V A

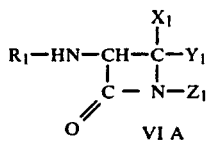

VI A wherein R' represents lower alkyl, aryl or aryl (lower alkyl), R'' represents hydrogen or lower alkyl or R' and R'' together with the carbon atoms to which they are attached represent lower cycloalkyl, R''' represents lower alkyl or a group —OR, wherein R represents lower alkyl, $X_1$, $Y_1$ and $Z_1$ are hydrogen or selected organic radicals and $R_1$ represents an acyl group; which successively involves reacting an 1,3-dicarbonyl compound of the formula:

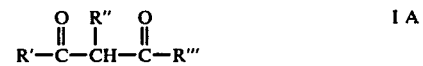

I A with glycine in the presence of a base to form a vinylamino salt of the formula:

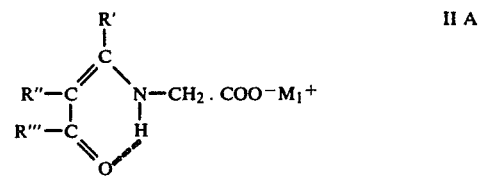

II A wherein $M_1{}^+$ is the cation of the base, activating the carboxyl group of said vinylamino salt with an appropriate activating agent and reacting the activated compound in the presence of a tertiary base with an imino compound of the formula:

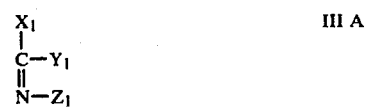

III A to form the corresponding α-vinylamino-β-lactam of formula IV A and if desired, subjecting said β-lactam to mild acid hydrolysis to obtain the corresponding α-amino-β-lactam of formula V A and if desired, acylating said α-amino-β-lactam with an appropriate acylating agent to obtain a corresponding α-acylamino-β-lactam of formula VI A.

24 Claims, No Drawings

PREPARATION OF β-LACTAMS AND INTERMEDIATES THEREFOR

PRIOR APPLICATION

This application is a continuation-in-part application of my copending commonly assigned U.S. patent application Ser. No. 969,207 filed Dec. 13, 1978, now abandoned.

BACKGROUND OF THE INVENTION

Penicillins and cephalosporins are β-lactam antibiotics which are widely used in medicine. There is continued interest, however, in obtaining new β-lactam variants to better combat strains of microorganisms that acquire resistance to antibiotics inculding commonly used penicillins and cephalosporins. Very recently new antibiotics, such as cephamycins and nocardicins have been discovered which are also β-lactam derivatives.

The last few years have seen great progress toward economically promising total synthesis of penicillins, cephalosporins and analogs and the key step in this process consists in reacting an α-azidoacyl chloride with an imino compound in the presence of a teritary amine to form an α-azido-β-lactam which may be monocyclic or polycyclic depending on the imino compound.

Bose and co-workers devised this synthetic method and effected the total synthesis of 6-epipenicillin and various penam and cephem derivatives (A. K. Bose, G. Spiegelman and M. S. Manhas, J. AM. Chem. Soc., 90, 4506 (1968)). The α-azido-β-lactam in each case obtained from an appropriate imino compound is reduced to an α-amino-β-lactam and modified in various ways to provide, α-amido-β-lactams (cis or trans), α-alkoxy-β-lactams, etc.

The α-azido-β-lactam approach has been used by several research groups for the total synthesis of various penicillins, cephalosporins, carba and oxa analogs of cephalosporins, isocephalosporin and its oxa-analogs, nocardicins, etc. (B. G. Christensen and R. W. Ratcliffe, Annual Reviews of Medicinal Chemistry, Chap. 28, 271 (1976)).

Although successful in the laboratory for the synthesis of a wide variety of monocyclic and polycyclic β-lactams, the α-azido-β-lactam method suffers from serious disadvantages for large scale production of α-amino-β-lactam compounds. Azidoacetic acid and azidoacetyl chloride have been reported to be prone to violent decomposition, especially during purification by distillation under reduced pressure of the latter and this purification is important for obtaining satisfactory β-lactam formation. The reduction of α-azido-β-lactam to α-amino-β-lactam is also a step that requires careful control to ensure a high yield of the desired product. Unexpected β-lactam cleavage reactions have been reported by Bose et al (J. Org. Chem., Vol. 38, (1973), p. 1238) during the catalytic reduction and subsequent acylation of α-azido-β-lactams. Therefore, it is desirable—in particular for large scale production—to develop an alternative approach to the synthesis of α-amino-β-lactams. The present invention consitutes such an approach.

Various protective groups have been devised in peptide chemistry to provide temporary protection to the amino group of an amino acid while the carboxy group of the same molecule is activated and utilized for amide bond formation. One such protective group described by Dane et al (Agnew Chem. Int. Ed. Vol. 1 (1962), p. 658) appeared to be of potential value to a synthesis of this type. In this method, an amino acid such as valine, alanine or phenyl-alanine is reacted with an 1,3-diketone or a β-ketoester in the presence of alkali to form a vinylamino acid salt (A), for example according to the following reaction scheme:

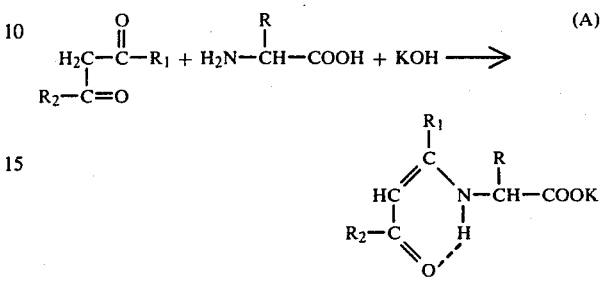

wherein R, $R_1$ and $R_2$ are selected organic radicals or hydrogen atoms.

The vinylamino acid salt (A) can be reacted with a chloroformate ester and an amino acid ester to form a protected dipeptide ester (C). Mild acid treatment of (C) removes the protective group to to provide a dipeptide ester (D):

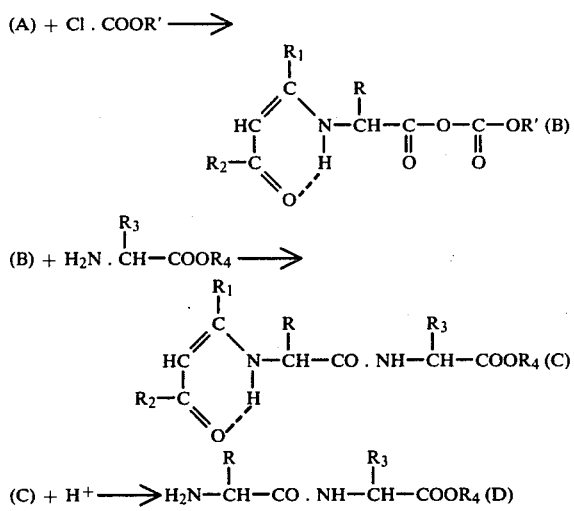

wherein $R_3$ is as defined above for R–$R_2$ and R' and $R_4$ are ester radicals.

Some of the diketones and β-ketoesters that are commonly used in the above method are shown in Table I.

TABLE I $$H_2C-\underset{R_2-C=O}{\overset{\overset{O}{\|}}{C}}-R_1$$

| | $R_1$ | $R_2$ |
|---|---|---|
| 1 | $CH_3$ | $OCH_3$ |
| 2 | $CH_3$ | $OC_2H_5$ |
| 3 | $CH_3$ | $OC(CH_3)_3$ |
| 4 | $CH_3$ | $CH_3$ |
| 5 | $C_6H_5$ | $CH_3$ |

Others are depicted in the following formulae:

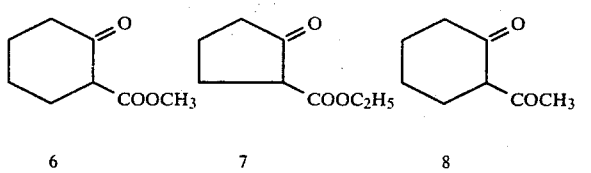

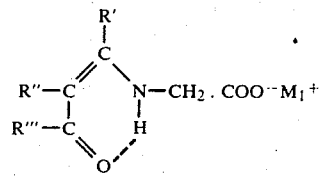

I attempted to react vinylamino acid salts of type (A) prepared from amino acids such as alanine, valine, phenylalanine, etc. with imino compounds such as benzalaniline via the mixed anhydride route but met with failure in obtaining any β-lactam.

Vinylamino ketones are known to be reactive and capable of undergoing various types of condensation reaction. Thus, a recent report (S. Auricchio, R. Bernardi and A. Ricca, Tetrahedron Letters; 4831–4834 (1976)) describes the formation of a substituted aniline as well as a pyridine derivative from 4-ethylamino-3-penten-2-one.

The reaction of vinylamino acid salts with alkyl chloroformates has been reported to produce 1,3-oxazolidin-5-ones in high yield (S. K. Gupta, Synthesis, 724 (1975)).

Vinylamino acid salts have been shown to react with trifluoracetic anhydride to give pyrrole compounds (S. K. Gupta, Synthesis, 726 (1975)).

In the light of the foregoing, it is fully unexpected that in the process of the present invention certain vinylamino salts of glycine can be reacted under selected conditions with certain imino compounds to form monocyclic and polycyclic β-lactams.

BACKGROUND OF THE INVENTION

It is an object of the invention to provide a novel process for the production of β-lactams in good yield using economical and safe reactants.

It is a further object of the invention to provide a novel process for the total synthesis of various monocyclic and polycyclic β-lactam antibiotics and their analogs including isopenicillins and isocephalosporins.

These and other objects and advantages of the invention will become obvious from the following detailed description.

THE INVENTION

The novel process of the invention for the preparation of β-lactams successively involves reacting an 1,3-dicarbonyl compound of the formula:

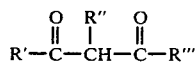

I A wherein R' represents lower alkyl, aryl or aryl (lower alkyl), R'' represents hydrogen or lower alkyl or R' and R'' together with the carbon atoms to which they are attached represent lower cycloalkyl and R''' represents lower alkyl or a group —OR, wherein R represents lower alkyl, with glycine in the presence of a base to form a vinylamino salt of the formula:

II A wherein $M_1^+$ is the cation of the base, activating the carboxyl group of said vinylamino salt with an appropriate activating agent and reacting the activated compound in the presence of a tertiary base with an imino compound of the formula:

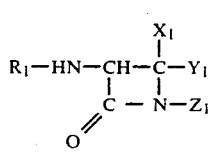

III A wherein $X_1$, $Y_1$ and $Z_1$ are hydrogen or selected organic radicals, to form the corresponding α-vinylamino-β-lactam of the formula:

IV A and if desired, subjecting said β-lactam to mild acid hydrolysis to obtain the corresponding α-amino-β-lactam of the formula:

V A and if desired, acylating said α-amino-β-lactam with an appropriate acylating agent to obtain a corresponding α-acylamido-β-lactam of the formula

VI A wherein $R_1$ represents an acyl groups of an organic carboxylic acid of 1 to 18 carbon atoms.

Suitable 1,3-dicarbonyl compounds of formula IA are, for example, those wherein R' is methyl and phenyl, R'' is hydrogen or R' and R'' together with the carbon atoms to which they are attached represent cyclopentyl or cyclohexyl and R''' is methyl or a group —OR, wherein R is methyl, ethyl or t.-butyl.

Particularly suitable are 1,3-dicarbonyl compounds of formula IA wherein R''' represents a group —OR, i.e. β-ketoesters of the formula

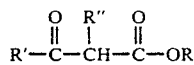

and especially preferred are those β-ketoesters wherein R' is methyl and R" is hydrogen, i.e. lower alkyl esters of acetoacetic acid, particularly methyl and ethyl acetoacetate.

The base $M_1OH$ present during the reaction between an 1,3-dicarbonyl compound of formula I A and glycine can be, for example an alkali metal hydroxide; particularly preferred is potassium hydroxide.

Suitable activating agents are, for example, lower alkyl haloformate esters, such as methyl, ethyl or t.-butyl chloroformate, di (lower alkyl) or diaryl phosphochloridates, such as diethyl or diphenyl phosphochloridate and cyanuric choride. Particularly preferred activating agents are methyl and ethyl chloroformate and cyanuric chloride.

The acyl radical of the organic carboxylic acid having 1 to 18 carbon atoms is preferably derived from an aliphatic, aromatic, cycloaliphatic or heterocyclic carboxylic acid. Examples of suitable acids are alkanoic acids, such as formic acid, acetic acid, propionic acid, butyric acid, isobutyric acid, valeric acid, isovaleric acid, trimethyl acetic acid, caproic acid, β-trimethyl propionic acid, heptanoic acid, caprylic acid, pelarginic acid, capric acid, undecylic acid, lauric acid, myristic acid, palmitic acid and stearic acid; alkenoic acids such as undecylenic acid and oleic acid; cycloalkyl carboxylic acids such as cyclopentyl carboxylic acid, cyclopropyl carboxylic acid, cyclobutyl carboxylic acid and cyclohexyl carboxylic acid; cycloalkyl alkanoic acids such as cyclopentyl acetic acid, cyclohexyl acetic acid, cyclopentyl propionic acid and cyclohexyl propionic acid; arylalkanoic acids such as phenyl acetic acid and phenyl propionic acid; aryl carboxylic acids such as benzoic acid and 2,4-dinitrobenzoic acid; phenoxy alkanoic acids such as phenoxy acetic acid, p-chlorophenoxy acetic acid, 2,4-dichlorophenoxy acetic acid, 4-ter-butyl-phenoxy acetic acid 3-phenoxy pripionic acid and 4-phenoxy butyric acid; heterocyclic carboxylic acids such as furane-2-carboxylic acid, 5-ter-butyl-furane-2-carboxylic acid, 5-bromofurane-2-carboxylic acid and nicotinic acids; β-ketoalkanoic acids, such as acetylacetic acid, propionylacetic acid and butyrylacetic acid, amino acids such as diethylaminoacetic acid and aspartic acid.

The activation reaction and the subsequent reaction with an imino compound of formula III A is carried out in the presence of a tertiary base such as pyridine or triethylamine, the latter base being preferred.

The imino compounds of formula III A can be a wide range of compounds such as aliphatic imines, cyclic imines, thioimidates, mono- and polycyclic compounds, etc. resulting in a wide variety of β-lactams. The $X_1$, $Y_1$ and $Z_1$ substituents may be hydrogen or any suitable organic radical, wherein any reactive groups are properly protected from the various reactants.

The substituents $Y_1$ and $Z_1$ together with the atoms to which they are attached may also form a ring system; in that case the reaction between a vinylamino salt of formula II A and the imino compounds of formula III A will result in bicyclic or polycyclic α-vinylamino-β-lactams of formula IV A, α-amino-β-lactams of formula V A and α-acylamido-β-lactams of formula VI A, such as penicillin or cephalosporin type compounds and isomers and analogs thereof, as well as other polycyclic systems, such as for example, tricyclic systems.

Preferred imino compounds of formula III A are, however, those compounds wheren $Y_1$ represents furyl, phenyl optionally substituted by methoxy or dimethylamino, styryl, optionally esterified carboxyl or hydroxymethylene, $X_1$ represents hydrogen or methylthio or $X_1$ together with $Y_1$ represents 1,5-pentylene and $Z_1$ represents hydrogen, methyl optionally substituted by phenyl, phenyl optionally substituted by halogen, methyl, methoxy, methylthio or dimethylamino, or $Z_1$ represents a group

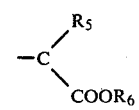

wherein $R_5$ represents an ethyl or ethylidene group optionally substituted by an optionally esterfied hydroxy group and $R_6$ represents a hydrogen atom or a carboxylic ester (preferably a p-nitrobenzyl) group.

It follows from the above paragraphs that the novel process of the invention thus particularly relates to the preparation of α-amino-β-lactams of the formula

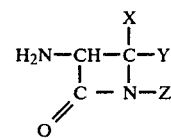

wherein Y represents furyl, phenyl optionally substituted by methoxy or dimethylamino, styryl, optionally esterified carboxyl, or hydroxymethylene, X represents hydrogen or methylthio or X together with Y represents 1,5-pentylene and Z represents hydrogen, methyl optionally substituted by phenyl, phenyl optionally substituted by halogen, methyl, methoxy, methylthio or dimethylamino, or Z represents a group

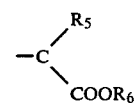

wherein $R_5$ represents an ethyl or ethylidene group optionally substituted by an optionally esterified hydroxy group and $R_6$ represents a hydrogen atom or a carboxylic ester (preferably a p-nitrobenzyl) group, by reacting an acetoacetate of the formula

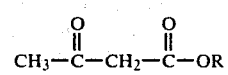

wherein R represents lower alkyl, with glycine in the presence of a base MOH, wherein M represents an alkali metal, to form a vinylamino salt of the formula

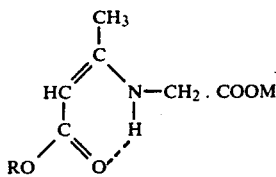

activating the carboxyl group of the compound obtained with an activating agent selected from the group consisting of lower alkyl haloformate esters, di(lower alkyl) or diaryl phosphochloridates and cyanuric chloride, and reacting the activated compound in the presence of a tertiary base with an imino compound of the formula

III wherein X, Y and Z are as defined hereinabove, to form the corresponding α-vinylamino-β-lactam of the formula

IV

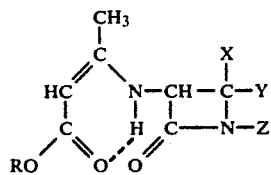

and if desired, subjecting the compound thus obtained to mild acid hydrolysis to form the corresponding α-amino-β-lactam of formula V, and if desired, acylating the compound thus obtained with an acylating agent to form a corresponding α-acylamido-β-lactam of the formula

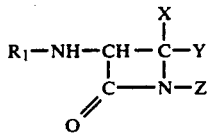

VI wherein $R_1$ represents an acyl group.

The reaction between a vinylamino salt of formula II and the activating agent is preferably carried out in an inert organic medium, such as dichloromethane or ether, at relatively low temperatures, for example −10° to −20° C., under a nitrogen atmosphere and in the presence of a tertiary base, such as triethylamine.

The reaction between the activated compound and an imino compound of formula III can usually be carried out in the same reaction medium, also without isolating the activated compound formed during the previous reaction step. The latter reaction is preferably carried out at ambient temperature or somewhat lower temperatures, for example 0° C.

The α-vinyl-amino-β-lactams of formulae IV and IV A, the α-amine-β-lactams of formulae V and V A and the α-acylamino-β-lactams of formulae VI and VI A have antibacterial activity and are convenient intermediates for the large scale production of known valuable β-lactam therapeutics.

For example 1-phenyl-3-phenoxyacetamido-4,4-spirocyclohexane-2-azetidinone and related compounds which can be prepared according to the process of the invention, have been disclosed in U.S. Pat. No. 3,546,211 to have anti-inflammatory activity.

Further, N-unsubstituted monocyclic β-lactams of the formula

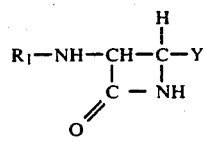

in particular where $R_1$ represents $C_6H_5O.CH_2.CO-$ and Y is phenyl, which according to British Pat. No. 1,301,720 are of value as lactamase inhibitors, can also be prepared according to the method of the invention.

The method of the invention can also be used to prepare 3-thienylacetamido-4tosyloxymethyl-2-azetidinone of the formula

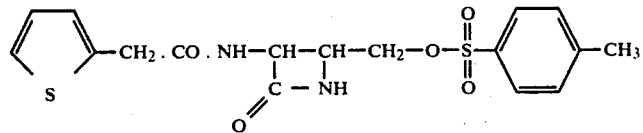

which was previously described by D. B. Bryan et al, J. Am. Chem. Soc., 99, 2353 (1977) and which is a key intermediate for the synthesis of the following S-2-isocephalosporin derivatives:

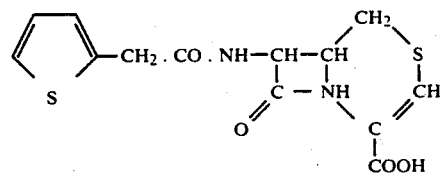

which is an example of an interesting new type of "isocephem" antiboitics as disclosed by T. W. Doyl et al, Can. J. Chem., 55, 468 (1977) and W. P. Huffman et al, J. Am. Chem. Soc. 99, 2353 (1977).

Another versatile intermediate which can be prepared accordingly to the process of this invention, is 3-phenoxyacetamido-4-carbomethoxy-2-azetidinone of the formula

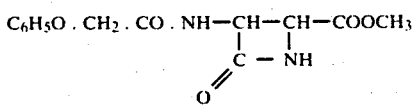

which can be used for the synthesis of the following 2-aza-1-desthiapenicillin derivative:

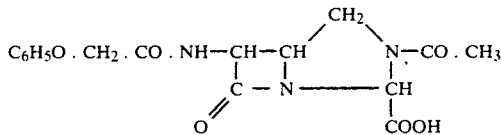

which is an example of a new class of "isopenicillin" antibiotics, as is disclosed by W. F. Huffman et al, J. Am. Chem. Soc., 99, 2352 (1977).

The above-identified N-unsubstituted β-lactam key intermediates are preferably prepared from corresponding suitably N-substituted β-lactams (such as, for example, N-veraryl-substituted β-lactams) by removal of the N-substituents in known manner, for example, by means of potassium persulfate ($K_2S_2O_8$) and sodium dihydrogen phosphate ($NaH_2PO_4.7H_2O$).

N-unsubstituted β-lactams can also be prepared starting from the corresponding α-acylamide-β-lactams of formula VI wherein Z represents a group

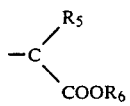

wherein $R_5$ and $R_6$ are as hereinbefore defined, for example by means of an excess of Jones reagent or by reaction with ruthenium tetroxide.

Similarly, β-lactams substituted in the 4-position by an (esterified) carboxyl group are preferably prepared by oxidation in known manner of a corresponding suitably 4-substituted β-lactam, such as 4-styryl-, 4-furano- or 4-phenyl-β-lactam. The oxidation can be carried out, for example, with potassium permanganate ($KMnO_4$), or ozone or $RuO_4$.

A 4-carboxy-β-lactam thus obtained can be esterified in usual manner, for example, with a solution of diazomethane in ether to afford the corresponding 4-carbomethoxy-β-lactam derivative.

EXAMPLE 1

(a) A solution of 2.8 g. of ethyl chloroformate in 10 ml. of dichloromethane was added dropwise to a mixture of 5.2 g. of potassium α-methyl-β-carbomethoxy-vinylamino-acetate (prepared by reacting methyl acetoacetate with glycine in the presence of potassium hydroxide) and 2.5 g. of triethylamine in 150 ml. of anhydrous ether, kept at −5° to −10° C. The resulting mixture was maintained at −5° C. for 20 minutes and then a solution of 5.0 g. of furfurylidene-p-anisidine and 2.5 g. of triethylamine in 50 ml. of dry ether and 20 ml. of dichloromethane was added dropwise with stirring over a period of 90 minutes. The reaction mixture was stirred for 2 hours at 0° C. and then for 10–12 hours at room temperature. Next the mixture was filtered and the solid on the filter washed with dichloromethane. The combined filtrates were washed with water and dried over anhydrous magnesium sulfate. After removal of the solvent and crystallization of the residue from dichloromethane/n.hexane there was obtained a product, melting at 174°–175° C., which according to the proton magnetic resonance spectrum was: cis-3-(α-methyl-β-carbomethoxy-vinylamino)-1-(p-methoxyphenyl)-4-furyl-2-azetidinone.

IR: 1760 (β-lactam CO), 1665 (α,β-unsaturated ester) cm$^{-1}$. NMR (CDCl$_3$): 6.28–7.48 (m, 8H), 5.3–5.0 (m, 2H), 4.49 (s, 1H), 3.71 (s, 3H), 3.52 (s, 3H), 1.90 (s, 3H).

(b) A mixture of 1.0 g. of the product of (a) in 15 ml. of acetone and 10 ml. of 2N hydrochloric acid was stirred for 15 minutes at room temperature and filtered. The filtrate was dissolved in water, neutralized with sodium hydrogen carbonate, extracted with dichloromethane, washed with water and dried over magnesium sulfate. Removal of the solvent under reduced pressure provided 600 mg. (82%) of cis-3-amino-1-(p-methoxyphenyl)-4-furyl-2-azetidinone; m.p. 129°–131° C. IR: 3570, 3345 (—NH$_2$), 1730 (β-lactam CO) cm$^{-1}$.

NMR (CDCl$_3$): 7.28–6.26 (m, 7H), 5.11 (d, J=5Hz, 1H), 4.38 (d, J=5Hz, ½H), 4.13 (d, J=5Hz, ½H), 3.65 (s, 3H), 1.37 (b, 2H).

(c) The acylation of this product with phenylacetyl chloride in the presence of triethylamine under standard conditions provided cis-1-(p-methoxyphenyl)-4-furyl-3-phenylacetamido-2-azetidinone.

EXAMPLE 2

(a) The imino compound (m.p. 109° C.), prepared from p-anisaldehyde and benzhydrylamine, was condensed with potassium α-methyl-β-carbomethoxy-vinylamino-acetate under the same general conditions as described in Example 1(a). The product thus obtained in 40% yield, was assigned the cis configuration on the basis of its proton magnetic resonance spectrum: cis-1-benzhydryl-4-(p-methoxyphenyl)-3-(α-methyl-β-carbomethoxy-vinylamino)-2-azetidinone; m.p. 134° C.

IR: 1750 (β-lactam CO), 1660 (α,β-unsaturated ester) cm$^{-1}$.

NMR (S): 1.75 (s, 3H), 3.55 (s, 3H), 3.8 (s, 3H), 4.35 (s, 1H), 4.85 (d, 1H), 5.05 (d, 1H), 5.75 (s, 1H), 6.75–7.35 (m, 14H), 8.7 (d, 1H).

(b) On treatment with 2N hydrochloric acid according to the method described in Example 1(b) the product of (a) in acetone was converted to cis-3-amino-1-benzhydryl-4-(p-methoxyphenyl)-2-azetidinone; m.p. 140° C.

IR: 1760 (β-lactam CO) cm$^{-1}$.

NMR: 3.65 (s, 3H), 4.4–4.9 (m, 2H), 5.6 (s, 1H), 6.6–7.4 (m, 14H).

(c) Acylation of the product of (b) with phenylacetyl chloride provided: cis-1-benzhydryl-3-phenylacetamido-4-(p-methoxyphenyl)-2-azetidinone.

IR- 1690 (—NH—CO), 1740 (β-lactam CO) cm$^{-1}$.

NMR: 3.75 (s, 3H), 4.25 (m, 2H), 4.95 (d, 1H), 5.5 (q, 1H), 5.8 (s, 1H), 6.5–7.4 (M, 20H).

EXAMPLE 3

(a) Using essentially the same method as described in Example 1(a), potassium α-methyl-β-carbomethyl-vinylamine-acetate was condensed with p-methoxybenzylidene-p-toluidine to provide in 52% yield: cis-4-(p-methoxyphenyl)-3-(α-methyl-β-carbomethoxy-vinylamino)-1-(p-tolyl)-2-azetidinone; m.p. 182° C.

(b) According to the method described in Example 1(b), the product of (a) was converted to cis-3-amino-4-(p-methoxyphenyl)-1-(p-tolyl)-2-azetidinone and this compound was directly acylated to:

cis-4-(p-methoxyphenyl)-3-phenylacetamido-1-(p-tolyl)-2-azetidinone; m.p. 175° C. and to:

cis-4-(p-methoxyphenyl)-3-phenoxyacetamido-1-(p-tolyl)-2-azetidinone; m.p. 176°–177° C.

(c) In the same way were prepared:

cis-3-(α-methyl-β-carbomethoxy-vinylamino)-1-(p-methoxyphenyl)-4-phenyl-2-azetidinone; m.p. 159°-160° C.

NMR (CDCl$_3$): 1.8 (s, 3H), 3.6 (s, 3H), 3.75 (s, 3H), 4.6 (s, 1H), 5.05 (d, 1H, J=6Hz), 5.25 (d, 1H, J=6Hz), 6.8-7.4 (b, 9H), 8.3 (b, 1H), cis-3-(α-methyl-β-carbomethoxy-vinylamino)-1,4-di(p-methoxyphenyl)-2-azetidinone; m.p. 129°-130° C.

NMR (CDCl$_3$): 1.9 (s, 3H), 3.5 (s, 3H), 3.75 (s, 3H), 3.8 (s, 3H), 4.4 (s, 1H), 5.05 (d, 1H, J=6Hz), 5.25 (d, 1H; J=6Hz), 6.8-7.4 (b, 8H), 8.5 (b, 1H).

cis-3-(α-methyl-β-carbomethoxy-vinylamino)-1-(p-N-dimethylaminophenyl)-4-phenyl-2-azetidinone; m.p. 129°-130° C.

cis-3-(α-methyl-β-carbomethoxy-vinylamino)-1-methyl-4-phenyl-2-azetidinone; m.p. 78°-80° C.

IR: 1750 (β-lactam CO), 1660 (α,β-unsaturated ester) cm$^{-1}$.

NMR: 1.8 (s, 3H), 2.85 (s, 3H), 3.5 (s, 3H), 4.35 (s, 1H), 4.8 (d, 1H), 5.1 (q, 1H), 7.4 (b, 5H), 8.5 (d, 1H).

cis-4-(p-N-dimethylaminophenyl)-1(p-methylthiophenyl)-3-(α-methyl-α-carbomethoxy-vinylamino)-2-azetidinone; m.p. 192°-193° C.

IR: 1750 (α-lactam CO), 1660 (α,β-unsaturated ester) cm$^{-1}$.

NMR: 1.87 (s, 3H), 2.15 (s, 3H), 2.95 (s, 6H), 3.5 (s, 3H), 4.4 (s, 1H), 5.05 (d, 1H), 5.25 (d, 1H), 6.6-7.4 (m, 9H).

(d) A solution of 0.01 mole of potassium α-methyl-β-carbomethoxy-vinylamino-acetate and 0.1 mole of diethyl phosphochloridate in 200 ml. of dichloromethane was stirred at room temperature under nitrogen atmosphere for 20 minutes. To this solution was added dropwise a solution of 0.1 mole of p-methoxybenzylidene-p-toluidine and 0.2 mole of triethylamine in 100 ml. of dichloromethane over a period of 1 hour. The stirring was continued overnight. The reaction mixture was then washed with water and dried over magnesium sulfate. Removal of the solvent followed by recrystallization from dichloromethane/n-hexane provided in 30% yield pure;

cis-4-(p-methoxyphenyl)-3-(α-methyl-β-carbomethoxy-vinylamino)-1-(p-tolyl)-2-azetidinone; m.p. 173°-174° C. IR: 1750 (β-lactam CO), 1655 (α,β-unsaturated ester) cm$^{-1}$.

NMR: 1.9 (s, 3H), 2.3 (s, 3H), 3.55 (s, 3H), 3,85 (s, 3H), 4.4 (s, 1H), 5.1 (d, 1H), 5.3 (d, 1H), 6.8-7.5 (m, 9H).

Similar results were obtained when diethyl phosphochloridate was substituted by diphenyl phosphochloridate.

(e) The procedure of (a) was repeated, but isobutyl chloroformate was substituted for ethyl chloroformate. The yield of the product of (a) was now 40%.

EXAMPLE 4

(a) According to the method described in Example 1(a) potassium α-methyl-β-carbethoxy-vinylamino-acetate (prepared by reacting ethyl acetoacetate with glycine in the presence of potassium hydroxide) was reacted with p-methoxybenzylidene-p-toluidine. There was obtained in 60% yield:

cis-3-(α-methyl-β-carboethoxy-vinylamino)-1-(p-tolyl)-4-(p-methoxyphenyl)-2-azetidinone; m.p. 129°-130° C.

IR: 1750 (β-lactam CO), 1658 (α,β-unsaturated ester) cm$^{-1}$.

NMR (S): 1.25 (t, 3H, J=8Hz), 1.85 (s, 3H), 2.35 (s, 3H), 4.1-3.75 (m, 5H), 4.45 (s, 1H), 5.2-5.45 (m, 2H), 6.9-7.5 (m, 9H). mol. peak in mass spectrum (m/e): 395.

(b) In the same way were prepared:

cis-3-(α-methyl-β-carbethoxy-vinylamino)-4-(p-N-dimethylaminophenyl)-1-(p-methylthiophenyl)-2-azetidinone IR (CH$_2$Cl$_2$): 1745 (β-lactam CO), 1650 (α,β-unsaturated ester) cm$^{-1}$.

NMR (CDCl$_3$): 1.15 (t, 3H, J=8Hz), 1.85 (s, 3H), 2.4 (s, 3H), 2.9 (s, 6H), 3.95 (q, 2H, J=8Hz), 4.45 (s, 1H), 5.0 (d, 1H, J=6Hz), 5.2 (d, 1H, J=6Hz), 6.6-7.3 (m, 8H), 8.5-8.7 (b, 1H).

cis-3-(α-methyl-β-carbethoxy-vinylamino)-1-(p-methoxyphenyl)-4-phenyl-2-azetidinone; m.p. 140° C.

IR: 1750 (β-lactam CO), 1655 (α, β-unsaturated ester)cm$^{-1}$.

NMR: 1.2 (t, 3H, J=7Hz), 1.9 (s, 3H), 2.75 (s, 3H), 3.95 (q, 2H, J=7Hz), 4.45 (s, 1H), 5.1 (d, 1H, J=6Hz), 5.3 (d, 1H, J=6Hz), 6.7-7.4 (m 9H), 8.5-8.65 (b, 1H).

cis-3-(α-methyl-β-carbethoxy-vinylamino)-1-(p-chlorophenyl)-4phenyl-2-azetidinone; m.p. 125°-127° C.

IR: 1750 (β-lactam CO), 1660 (α,β-unsaturated ester) cm$^{-1}$.

NMR: 1.25 (t, 3H, J=7Hz), 1.9 (s, 3H), 3.95 (q, 2H, J=8Hz), 4.45 (s, 1H), 5.25 (d, 1H, J=6Hz), 5.35 (d, 1H, J=6Hz), 7.2-7.45 (m, 9H), 8.5-8.7 (b, 1H).

EXAMPLE 5

(a) A mixture of 2.1 g. (0.01 mole) of potassium α-methyl-β-carbomethoxy-vinylamino-acetate and 1 g. (0.01 mole) of triethylamine in 150 ml. of dry dichloromethane was cooled to −10° C. and 1.2 g. (0.01 mole) of ethyl chloroformate was added dropwise over a period of 30 minutes with constant stirring under nitrogen atmosphere. The mixture was stirred for an additional hour followed by the dropwise addition over a period of 1 hour of a solution of 2.3 g. (0.01 mole) of methyl N-phenylbenzthioimidate (prepared by methylation of thiobenzamide) and 1 g. (0.01 mole) of triethylamine in 100 ml. of dichloromethane. The resulting mixture was stirred for 2 hours at 0° C. and allowed to stand overnight at room temperature. The reaction mixture was then washed with water and dried over magnesium sulfate. The solvent was evaporated and the residue chromatographed over Florisil using dichloromethane/n. hexane (20:80) as the eluent. The unreacted thiomidate was eluted first, followed by the desired product using dichloromethane as the eluent. There was obtained in 41% yield:

cis-3-(α-methyl-β-carbomethoxy-vinylamino)-1.4-diphenyl-4-methylthio-2-azetidinone; m.p. 172°-173° C.

IR (nujol): 1750 (β-lactam CO), 1655 (α,β-unsaturated ester) cm$^{-1}$.

NMR (CDCl$_3$): 2.0 (s, 2H), 5.3 (d, 1H, J=10Hz), 7.15-7.9 (m, 10H), 8.3 (d, 1H, J=10Hz).

(b) The product of (a) was stirred with 10 ml. of concentrated hydrochloric acid for 20 minutes while the contents were cooled in a cold water bath. The desired product separated slowly; 40 ml. of acetone were added for complete precipitation. The product was separated by filtration and dried and used as such for the next step. There was obtained in 80% yield:

cis-3-amino-1,4-diphenyl-4-methylthio-2-azetidinone hydrochloride.

(c) A solution of 1 g. of phenylacetyl chloride in 50 ml. of dichloromethane was added dropwise over 20 minutes to a mixture of 1 g. of the product of (b) and 1 g. of triethylamine in 100 ml. of dichloromethane. The reaction mixture was stirred overnight, washed with water and dried over magnesium sulfate. The solvent was removed under reduced pressure and the residue crystallized from dichloromethane/n-hexane.

There was obtained 0.65 g. (51%) of:

cis-1,4-diphenyl-3-phenylacetamido-4-methylthio-2-azetidinone; m.p. 142° C.

IR: 1760 ($\beta$-lactam CO), 1640 (—NH—CO) cm$^{-1}$.

NMR (CDCl$_3$): 2.1 (s, 3H), 3.35 (s, 2H), 5.7 (d, 1H), 6.7-7.9 (m, 1H).

EXAMPLE 6

Using essentially the same method as described in Example 5(a), benzalaniline was condensed with potassium $\beta$-methyl-$\beta$carbomethoxy-vinylamino-acetate to provide:

cis-1,4-diphenyl-3-($\alpha$-methyl-$\beta$-carbomethoxy-vinylamino)-2-azetidinone; m.p. 160°-163° C.

IR: 1740 ($\beta$-lactam CO), 1660 ($\alpha,\beta$-unsaturated ester) cm$^{-1}$.

NMR (CDCl$_3$): 1.9 (s, 3H), 3.45 (s, 3H), 4.4 (s, 1H), 5.1 (d, 1H, J=6Hz), 5.35 (d, 1H, J=6Hz), 7.35 (b, 10H), 8.55 (d, 1H).

EXAMPLE 7

In the same way p-N-dimethylaminobenzylidene-aniline was condensed with potassium $\alpha$-methyl-$\beta$-carbomethoxy-vinylamido-acetate to provide:

cis-4-(p-N-dimethylaminophenyl)-1-phenyl-3-($\alpha$-methyl-$\beta$-carbomethoxy-vinylamino)-2-azetidinone; m.p. 128°-130° C.

IR: 740 ($\beta$-lactam CO), 1660 ($\alpha,\beta$-unsaturated ester) cm-$^{1}$.

NMR: 1.9 (s, 3H), 2.95 (s, 6H), 3.5 (s, 3H), 4.45 (s, 1H), 5.1 (d, 1H), 5.25 (d, 1H), 6.65-7.45 (m, 10H).

EXAMPLE 8

(a) A solution of 0.13 mole of ethyl chloroformate in 40 ml. of dichloromethane was added dropwise to a mixture of 0.13 mole of potassium $\alpha$-methyl-$\beta$-carbomethoxy-vinylamino-acetate and 0.13 mole of triethylamine in 150 ml. of anhydrous ether kept at −15° to −20° C. The resulting mixture was maintained at this temperature for 20 minutes. Then a solution of 0.01 mole of cyclohexylidine aniline and 0.01 mole of triethylamine in dichloromethane was added dropwise over a period of 1 hour.

The reaction mixture was stirred at −15° −20° C. for 2 hours and left overnight. After the usual work up procedure there was obtained:

cis-1-phenyl-4,4-spirohexane-3-($\alpha$-methyl-$\beta$-carbomethoxy-vinylamino)-2-azetidinone; m.p. 158° C.

IR: 1740 ($\beta$-lactum CO), 1660 ($\alpha, \beta$-unsaturated ester) cm$^{-1}$.

NMR: 2.15 (s, 3H), 1.2-2.1 (m, 10H), 3.7 (s, 3H), 4.55 (d, 1H, J=8Hz), 4.7 (s, 1H), 7.1-7.7 (m, 5H), 8.3 (d, 1H, J=8Hz).

(b) The product such obtained was reacted with acetone/HCl to provide:

cis-3-amino-1-phenyl-4,4-spirohexane-2-azetidinone hydrochloride; m.p. 223° C.

IR: 1760 ($\beta$-lactam CO) cm$^{-1}$.

NMR (DMSO-d$_6$): 1.3-2.3 (m, 10H), 2.5 (b, 2H), 6.6 (5, 1H), 7.1-7.6 (m, 5H).

(c) The amine hydrochloride was acylated with phenoxyacetyl chloride to provide:

cis-1-phenyl-3-phenoxyacetamido-4,4-spirohexane-2-azetidinone; m.p. 142° C.

IR: 3500 (—NH), 1765 ($\beta$-lactam CO), 1660 (—NH—CO) cm$^{-1}$.

NMR: 1.3-2.0 (m, 10H), 4.55 (s, 2H), 5.1 (d, 1H), 6.9-7.6 (m, 11H).

EXAMPLE 9

(a) Using essentially the same method as described in Example 8(a) there was prepared:

1-veratryl-3-($\alpha$-methyl-$\beta$-carbomethoxy-vinylamino)-4-($\beta$-styryl)-2-azetidinone (oil).

IR: 2900, 1755, 1720, 1250 cm$^{-1}$.

NMR (CDCl$_3$): 1.9 (s, 3H), 3.7 (s, 3H), 3.9 (s, 6H), 4.35 (dd, 1H, J=4.5Hz, J'=9Hz), 6.05 (dd, 1H, J=9Hz, J=16Hz), 6.7 (s, 1H), 6.85 (d, 1H, J=16 Hz), 6.9 (s, 3H), 7.35 (s, 5H), 9.1 (d, 1H, J=9Hz).

(b) This product was hydrolysed in the manner described hereinabove using p-toluenesulfonic acid monohydrate to provide the p-toluenesulfonic acid salt of the corresponding amino compound: 3-amino-1-veratryl-4-($\beta$-styryl)-2-azetidinone, which was acylated with phenoxyacetyl chloride and triethylamine to afford:

1-veratryl-4-($\beta$-styryl)-3-phenoxyacetamido-2-azetidinone

IR- 1750 ($\beta$-lactam CO), 1760 (—NH—CO) cm$^{-1}$.

NNR (CDCl$_3$): 3.85 (s, 3H), 3.9 (s, 3H), 4.4 (dd, 2H, J=15Hz, J'=48Hz), 4.5 (s, 2H), 5.4 (dd, 1H, J=5Hz, J=9Hz), 5.95 (dd, 1H, H=7.5Hz, J=16Hz), 6.6 (d, 1H, J=Hz), 6.8.

(c) A solution of 4.7 mmole of potassium persulfate (K$_2$S$_2$O$_8$) and 2.4 mmole of sodium dihydrogen phosphate (NaH$_2$PO$_4$.7H$_2$O) in 10 ml. of water was added to the refluxing solution of 1.2 mmole of the product of (b) in 50 ml. of 40% aqueous acetonitrile and the reaction was monitored through thin layer chromatography (TLC). After 30 minutes the reaction mixture was concentrated in vacuum and the aqueous phase extracted with 2 100 ml. portions of dichloromethane. The organic phase was washed with 50 ml. of 1N HCl, brine solution and dried over Na$_2$SO$_4$. The solvent was evaporated and the residue crystallized from anhydrous ether to provide in 20% yield white crystals of:

4-($\beta$-styryl)-3-phenoxyacetamido-2-azetidinone.

(d) To a mixture of 0.2 mmole of the product of (c) in 5 ml. of 60% aqueous acetone and 6 drops of dioxane was added 0.4 mmole of KMnO$_4$ and the mixture was stirred for 2 hours at room temperature, while the reaction was monitored through TLC. The reaction mixture was then filtered, layered with 40 ml. of ethyl acetate and acidified with 20 ml. of 1HCl. The organic layer was separated, dried over Na$_2$SO$_4$ and stripped of solvent to provide the crude acid which was dissolved in 5 ml. of dichloromethane and esterified with diazomethane in 3 ml. of ether. After stirring for 5 minutes, the solution was concentrated in vacuum and the product was purified by preparative TLC to obtain in 28% yield:

3-phenoxyacetamido-4-carbomethoxy-2-azetidinone; m.p. 138°-139° C. (lit. 140°-141° C.).

IR:3200-3250 (—NH), 1770 ($\beta$-lactam CO), 1740 (COOCH$_3$), 1675 (—NH—CO) cm$^{-1}$.

NMR: 3.6 (s, 3H), 4.45 (d, 1H), 4.48 (s, 2H), 5.63 (dd, 1H), 6.8-7.4 (m, 7H).

EXAMPLE 10

(a) The p-toluenesulfonic acid salt of 3-amino-1-veratryl-4-($\beta$-styryl)-2-azetidinone (preparedaccording to the method described in Example 9(a)–(b)) in 100 ml. of dichloromethane was treated with 23 mmoles of triethylamine to neutralise the p-toluenesulfonic acid. Then 13.8 mmoles of triethylamine were added followed by dropwise addition of 13.8 mmoles of phenylacetyl chloride in 20 ml. of dichloromethane.

The reaction mixture was stirred overnight. After the usual work up procedure there was obtained in 55.6% yield:

3-penylacetamido-1-veratryl-4-($\beta$-styryl)-2-azetidinone.

IR ($CH_2Cl_2$): 3100 (—NH), 1760 ($\beta$-lactam CO), 1665 (—NH-CO) $cm^{-1}$.

NMR ($CDCl_3$): 3.6 (s, 2H), 3.85 (s, 3H), 3.9 (s, 3H), 4.3 (d, 2H, J=36 Hz), 4.4 (dd, 1H, J=5 Hz, J'=7.5 Hz), 5.4 (dd, 1H, J=5 Hz, J'=9 Hz), 5.9 (dd, 1H, J=15 Hz, J'=7.5 Hz), 6.6 (d, 1H, J=15 Hz), 6.8 (s, 3H), 7.15 (s, 5H), 7.3 (m, 5H).

(b) To a solution of 0.7 mmole of the product of (a) in 10 ml. of 60% aqueous acetone was added 1.4 mmole of $KMnO_4$ and the mixture was stirred overnight. The solution was filtered and the filtrate concentrated to the aqueous phase, layered with 25 ml of ethyl acetate and then acidified with 15 ml. of 1 N CHl. The organic phase was separated and the aqueous phase extracted with ethyl acetate. The combined organic layers were dried and concentrated under vacuum. The crude 4-carboxy-1-veratryl-3-phenylacetamido-2-azetidinone was esterified with 10 drops of a solution of diazomethane in ether to provide in 18.3% yield; 4-carbomethoxyl-1-veratryl-3-phenylacetamido-2-azetidinone.

IR ($CH_2Cl_2$): 3200 (—NH), 1755 ($\beta$-lactam CO), 1730 ($COOCH_3$), 1660 (—NH—CO) $cm^{-1}$.

NMR ($CDCl_3$): 3.6 (s, 2H), 3.7 (s, 2H), 3.9 (s, 9H), 4.2 (d, 1H, J=6 Hz), 4.5 (dd, 1H, J=6 Hz, J'=10 Hz), 6.9 (m, 3H), 7.35 (m, 5H), 7.7 (d, 1H, J=10 Hz).

(c) A suspension of 0.133 mmole of the product of (b), 0.5 mmole of potassium persulfate and 0.26 mmole of sodium dihydrogen phosphate in 25% aqueous acetonitrile was refluxed for 10 minutes while the reaction was monitored throgh TLC. The acetonitrile was then stripped of under vacuum and the remaining aqueous phase was extracted with three 20 ml. portions of dichloromethane. The combined extracts were dried and concentrated to an oil which was purified through preparative TLC to provide in 37.2% yield:

4-carbomethoxy-3-phenylacetamido-2-azetidinone (oil).

IR ($CH_2Cl_2$): 3300 (—NH), 1755 ($\beta$-lactam CO), 1730 ($COOCH_3$), 1660 —NH—CO) $cm^{-1}$.

NMR ($CDCl_3$): 3.6 (s, 2H), 3.85 (s, 3H), 4.7 (d, 1H, J=5), 5.4 (m, 1H), 7.35 (m, 6H), 7.85 (d, 1H) J=9Hz).

EXAMPLE 11

(a) 3-Amino-1-veratryl-4-($\beta$-styryl)-2-azetidinone (obtained according to the procedure described in Example 9(a)–(b)) was acylated in manner described above with 3-thienylacetyl chloride to provide in 55% overall yield:

1-veratryl-4-(62 styryl)-3-thienylacetamido-2-azetidinone; (oil).

IR: 3150–3200 (—NH), 1750 ($\beta$-lactam CO), 1660 (—NH—CO) $cm^{31\ 1}$.

NMR ($CDCl_3$): 3.7 (s, 2H), 3.75 (s, 3H), 3.8 (s, 3H), 4.3 (dd, 2H, J=14 Hz, J'=54 Hz), 4.35 (dd, 1H, J=5.5 Hz, J'=8 Hz), 5.3 (dd, 1H, J'=5.5 Hz, J'=8 Hz), 5.8 (dd, 1H, J=8 Hz, J'=15 Hz), 6.5 (d, 1H, J=15 Hz), 6.8–7.3 (m, 11H), 7.4 (m, 1H).

(b) A mixture of 1.2 mmole of the product of (a) in 50 ml. of 40% aqueous acetonitrile, 4 mmoles of $K_2S_2O_8$ and 2 mmoles of $Na_2HPO_4.7H_2O$ was refluxed while the reaction was monitored through TCL. After 1 hour the mixture was concentrated to the aqueous phase which was extracted with two 100 ml. portions of dichloromethane. The organic phase was washed with 50 ml. of 1 N HCl, brine solution and dried over $Na_2SO_4$. The solution was concentrated to an oil which on trituration with ether provided in 17.5% yield:

4-($\beta$-styryl)-3-thienylacetamido-2-azetidinone: m.p. 217°–218° C.

IR: 3300–3200 (—NH), 1750 ($\beta$-lactam CO), 1665 (—NH—CO) $cm^{-1}$. NMR (DMSO-$d_6$): 3.4 (s, 2H), 4.2 (dd, 1H, J=4.5, J'=7 Hz), 5.0 (dd, 1H, J=4.5 Hz, J'=7.5 Hz), 6.0 (dd, 1H, J=7 Hz, J'=16 Hz), 6.2 (d, 1H, J=16 Hz), 6.7–7.2 (m, 8H), 8.35 (s, 1H), 8.6 (d, 1H, J=7.5 Hz).

(c) To a mixture of 0.4 mmole of the product of (b) in 10 ml. of 60% aqueous acetone and 2 ml. of dioxane was added 0.8 mmole of potassium permanganate and the mixture was stirred for 2 hours. The mixture was then filtered, concentrated to the aqueous phase which was layered with 80 ml. of ethyl acetate and acidified with 40 ml. of 1 N hydrochloric acid. The organic layer was separated, dried over $Na_2SO_4$ and concentrated to a crude oil. The oil was dissolved in dichloromethane and 0.6 ml. of diazomethane in ether was added. The mixture was stirred for 15 minutes at room temperature. The solvent was then evaporated and the desired product obtained by preparative TLC. This provided:

3-thienylacetamido-4-carboxymethoxy-2-azetidinone.

IR ($CH_2Cl_2$): 3150 –3200 (—NH), 1770 ($\beta$-lactam CO), 1740 ($COOCH_3$), 1660 (—NH—CO) $cm^{-1}$.

MNR ($CDCl_3$): 3.48 (s, 2H), 3.6 (s, 3H), 4.3 (d, 1H, J=5 Hz), 5.5 (dd, 1H, J=5 Hz, J'=9 Hz), 6.8–7.4 (m, 4H), 7.7 (s, 1H).

(d) To a cooled solution (0° C.) of 0.1 mmole of the product of (c) in 2 ml. of 75% aqueous tetrahydrofuran was added 1 mmole of sodium borohydride. The solution was stirred for 45 minutes at 0° C. and then acidified with 1 N HCl. The reaction mixture was concentrated to the aqueous phase which was extracted with 10 ml. of dichloromethane. The organic layer was washed with brine solution, dried over $Na_2SO_4$ and the solvent was evaporated under vacuum. The crude residue, consisting of 3-thienylacetamido-4-hydroxymethylene-2-azetidinone, was dissolved in 5 ml. of anhydrous dichloromethane and 0.1 mmole of pyridine was added. The mixture was cooled to 0° C. and then 0.1 mmole of p-toluenesulfonyl chloride was added. The mixture was stirred while the temperature was allowed to rise to room temperature. After 2 hours the mixture was washed with 10 ml of 5% aqueous $NaHCO_3$ and 20 ml. of brine solution. The organic phase was dried over $Na_2SO_4$ and the solvent was evaporated to give an oil which on purification provided in 40% yield:

3-thienylacetamido-4-tosyloxymethyl-2-azetidinone.

IR: 3200 (—NH), 1755 ($\beta$-lactam CO), 1655 (—NH—CO) $cm^{-1}$.

NMR ($CDCl_3$): 2.4 (s, 3H), 3.6 (s, 2H), 3.6–3.8 (m, 3H), 5.05 (dd, 1H, J=4.5 Hz, J'=7.5 Hz), 7.0–7.9 (M, 7H), 8.4 (s, 1H), 8.8 (d, 1H, J=7.5 Hz).

EXAMPLE 12

(a) According to the method described in Example 8(a) there was prepared in 65% yield:

1-veratryl-3-(α-methyl-β-carbomethoxy-vinylamino)-4-phenyl-2-azetidinone; m.p. 155°–156° C.

IR: 1740 (β-lactam CO), 1655 (α,β-unsaturated ester) cm$^{-1}$.

NMR: 1.7 (s, 3H), 3.4 (s, 3H), 3.7 (s, 3H), 3.8 (s, 3H), 4.25 (s, 1H), 4.6–5.2 (m, 4H), 6.7–7.4 (m, 8H), 8.5 (d, 1H).

mol. peak in mass spectrum (m/e): 410.

(b) The product of (a) was hydrolysed in manner described hereinbefore to provide:

3-amino-1-veratryl-4-phenyl-2-azetidinone, which was used as such in the next step.

(c) A solution of 10 mmoles of the product of (b) in 15 mmoles of triethylamine and 15 ml. of tetrahydrofuran was stirred for 15 minutes. Then 10 mmoles of phenoxyacetyl chloride were added to the cooled solution and the reaction mixture was stirred for 3 hours. The mixture was filtered through Celite while washing 3 times with tetrahydrofuran. The combined tetrahydrofuran extracts were concentrated in vacuum and the crude residue was purified by chromatography and crystallized from ether/dichloromethane. There was obtained:

1-veratryl-3-phenoxyacetamido-4-phenyl-2-azetidinone; m.p. 130° C.

IR: 1750 (β-lactam CO), 1660 (—NH—CO) cm$^{-1}$.

NMR: 3.8 (s, 3H), 3.9 (s, 3H), 4.3 (q, 2H), 4.9 (s, 2H), 5.05 (d, 1H), 5.7 (q, 1H), 6.7–7.6 (m, 14H).

(d) A solution of 4.7 mmoles of $K_2S_2O_8$ and 2.4 mmoles of $Na_2HPO_4.7H_2O$ in 10 ml. of water was added to the refluxing solution of the product of (c) in 60 ml. of 40% aqueous acetonitrile and the reaction mixture was refluxed for 1 hour. The mixture was then concentrated in vacuum and the aqueous phase was extracted with two 100 ml. portions of dichloromethane. The organic phase was washed with 1 N HCl, brine solution and dried over $Na_2SO_4$. The solvent was evaporated and the residue crystallized from ether to provide in 25% yield:

3-phenoxyacetamido-4-phenyl-2-azetidinone; m.p. 134°–136° C.

IR: 3250 (—NH), 1765 (β-lactam CO), 1680 (—NH—CO) cm$^{-1}$.

NMR: 4.25 (dd, 2H, J=15 Hz), 5.05 (d, 1H, J=4 Hz), 5.6 (q, 1H), 6.5–7.4 (m, 12H).

EXAMPLE 13

(a) A solution of crude 3-amino-1-veratryl-4-phenyl-2-azetidinone (prepared according to the method described in Example 12 (a)–(b)) and triethylamine in tetrahydrofuran was stirred for 15 minutes. Then an equimolar quantity of phenylacetyl chloride was added, while cooling. After the usual work up procedure there was obtained:

1-veratryl-3-phenylacetamido-4-phenyl-2-azetidinone; m.p. 164°–166° C.

IR: 3200 (—NH), 1760 (β-lactam CO), 1670 (—NH—CO) cm$^{-1}$.

NMR: 3.15 (s, 3H), 4.35 (q, 2H), 4.7 (d, 1H), 5.35 (q, 1H), 6.6–7.5 (m, 13H), 8.61 (d, 1H).

(b) The product of (a) was converted according to the method described in Example 12 (d) into:

3-phenylacetamido-4-phenyl-2-azetidinone; m.p. 187°–188° C. (lt.; m.p. 188° C.).

EXAMPLE 14

(a) According to the method described in Example 8(a) there was prepared in 50% yield:

1-veratryl-4-furyl-3-(α-methyl-β-carbomethoxy-vinylamino)-2-azetidinone; m.p. 116° C.

IR: 1740 (β-lactam CO), 1640 (α,β-unsaturated ester) cm$^{-1}$.

NMR: 1.8 (s, 3H), 3.55 (s, 3H), 3.83 (s, 3H), 3.86 (s, 3H), 4.45 (s, 1H), 4.6 (d, 1H), 4.7 (q, 2H), 5.1 (d, 1H), 6.4–7.7 (m, 6H), 8.7 (d, 1H).

mol. peak in mass spectrum (m/e): 400.

(b) The product of (a) was hydrolysed under acidic conditions in the usual manner to provide: 3-amino-1-veratryl-4-furyl-2-azetidinone which was used as such in the next reaction step.

(c) A solution of 0.01 mole of the product of (b) and 0.015 mole of triethylamine in 15 ml. of tetrahydrofuran was stirred for 15 minutes. Then 0.01 mole of phenylacetyl chloride was added to the mixture, while cooling and the mixture was stirred for 3 hours. Then it was filtered through Celite and washed 3 times with tetrahydrofuran. The combined extracts were evaporated under vacuum and the crude residue was purified by chromatography to provide in 60% yield:

1-veratryl-3-phenylacetamido-4-furyl-2-azetidinone; m.p. 138° C.

IR: 3150 (—NH), 1745 (β-lactam CO), 1640 (—NH—CO) cm$^{-1}$.

NMR: 3.5 (s, 2H), 3.75 (s, 3H), 3.8 (s, 3H), 4.2 (q, 2H), 4.7 (d, 1H), 5.6 (q, 1H), 6.0–7.5 (m, 12H).

mol. peak in mass spectrum (m/e): 420.

EXAMPLE 15

(a) 39.0 g. (328 mmoles) of d-threonine and 22.02 g. (393 mmoles) of potassium hydroxide were dissolved in 700 ml. of absolute methanol and the mixture was stirred at room temperature until it became homogeneous. Then 41.82 g. (361 mmoles) of methyl acetoacetate were added and the solution was stirred overnight. This solution was concentrated to dryness under reduced pressure and the resulting white solid recrystallized from absolute ethanol to yield 78.2 g. of the potassium salt of N-(α-methyl-β-carbomethoxyvinyl)-d-threonine. This solid was then suspended in 500 ml. of dichloromethane and stirred vigorously for 1 hour. The suspended material was filtered off and dried to yield 76.13 g. (91.0%) of the pure salt; m.p. 133°–135° C.

Analysis: calculated for $C_9H_{14}NO_5K$: C 42.35; H 5.49; N 5.49. found: C 42.61; H 5.78; N 5.31.

(b) 21.6 g (100 mmoles) of p-nitrobenzyl bromide and 25.5 g. (100 mmoles) of the product of (a) were dissolved in 100 ml. of anhydrous dimethylformamide and the solution was stirred at room temperature for 24 hours. The reaction mixture was then diluted with 300 ml. of ethyl acetate, washed with a saturated sodium bicarbonate solution and with brine and dried over sodium sulfate. The mixture was then concentrated in vacuo to yield 36.5 g of p-nitrobenzyl-d-threonine as a viscous oil. This material (quite pure according to thin layer chromatography) was dissolved in 80 ml. of 1,4-dioxane to which was added 19.02 g. (100 mmoles) of p-toluene sulfonic acid monohydrate. After stirring at room temperature for 20 hours, the product precipitated from the solution, was filtered, washed with ether and dried to yield 36.04 g. (84% in relation to the product of (a)) of p-nitrobenzyl-d-threonine p-toluenesulfonate as a white, fluffy solid; m.p. 142°–143° C.

Analysis: calculated for $C_{18}H_{22}N_2O_8S$: C 61.36; H 6.25; N 7.95. found: C 61.55; H 6.48; N 7.81.

By using a similar sequence of reactions p-nitrobenzyl-dl-threonine p-toluenesulfonate was synthesized starting from dl-threonine. The free threonine esters can be generated by treating the above salts with a base, such as an aqueous potassium carbonate solution or triethylamine.

(c) To a solution of p-nitrobenzyl-d-threonine in dry dichloromethane was added an equimolar amount of trans-cinnamaldehyde. The solution was refluxed for 5 minutes and then stirred for 1 hour at room temperature. To remove the water formed in the reaction mixture a quantity of molecular sieve was added and the mixture was stirred for another 1½ hours. The clear solution obtained by filtering of the reaction mixture was evaporated and the residual yellow oil was triturated with petroleum ether to obtain crude cinnamylidene N-(1-p-nitrobenzyloxycarbonyl-2-hydroxy-propyl) amine which was recrystallized from ethyl acetate/petroleum ether to obtain the pure product (87%); m.p. 98°–99° C.

IR (CHCl$_3$): 3100, 1750, 1625 cm$^{-1}$;

NMR (CDCl$_3$): 1.20 (d, 3H, J=7 Hz) 2.80 (s, broad, 1H), 3.85 (d, J=7 Hz, 1H), 4.35 (m, 1H), 5.25 (s, 2H), 7.00 (d, 2H) 7.2→7.6 (m, 7H) 8.20 (d, 8H, J=Hz, 3H).

CIMS: calculated: MW=368. found: M+1=369.

(d) To a suspension of 2.96 g. (14 mmoles) of potassium α-methyl-β-carbomethoxy-vinylamino-acetate in 120 ml. of anhydrous ether were added under anhydrous conditions 3.6 m. (28 mmoles) of triethylamine at $-25°$ C. Then 1.4 ml. (14 mmoles) of ethyl chloroformate was added dropwise and the reaction mixture was stirred for 30 minutes. To this mixture was added a solution of the product of (c) in 120 ml. of dry dichloromethane over a period of 30 minutes at $-25°$ C. The mixture was kept for 1 hour at room temperature and then evaporated to dryness under reduced pressure, triturated with anhydrous ether, cooled and filtered. The solid residue was extracted with chloroform; and chloroform solution was washed with water, dried and evaporated to dryness. The residual solid on crystallization from chloroform/ether gave 1.30 g. (26%) of colorless crystalline cis-1-(1'-p-nitrobenzyloxycarbonyl-2'-hydroxypropyl)-3-(α-methy-β-carbomethoxy-vinylamino)-4-styryl-2-azetidinone; m.p. 148°–150° C. (Average yield in several preparations ranged from 26–30%).

IR (nujol): 3400, 1750, 1725, 1650 cm$^{-1}$.

NMR (CDCl$_3$): 1.30 (d, 3H), 1.95 (s, 3H), 3.53 (s, 3H), 2.85 (s, 1H), 4.40 (two, q, overlapped, 2H) 4.55 (d, 2H), 5.10 (dd, 1H, J=5Hz J=9Hz), 5.30 (s, 2H), 6.15 (dd, 1H, J=9Hz, J'=16 Hz), 6.80, (d, 1H, J=16 Hz), 7.2→7.45 (m5H), 7.60 (d, 2H, J=9Hz), 8.20 (d, 2H J=9Hz), 9.15 (d, 1H, J=9Hz).

CIMS: calculated: MW=523. found: M+1=524.

(e) To a suspension of 3.98 g. (7.6 mmoles) of the product of (d) in 20 ml. of dry acetone was added 1.44 g (7.6 mmoles) of p-toluenesulfonic acid monohydrate at room temperature. The reaction mixture was stirred for 1 hour when the p-toluenesulfonic acid salt of cis-3-amino-1-(1'-p-nitrobenzyloxycarbonyl-2'-hydroxy-propyl)-4-styryl-2-azetidinone separated as a solid. Ether was added to the mixture which was cooled and filtered to obtain the pure salt. This product was suspended in 50 ml. of dry dichloromethane to which was added 0.9 ml. (8.6 mmoles) of triethylamine. After stirring for 1 hour the reaction mixture was washed twice with water, dried over sodium sulfate and evaporated to obtain solid cis-3-amino-1-(1'-p-nitrobenzyloxycarbonyl-2'-hydroxy-propyl)-4-styryl-2-azetidinone. This product was dissolved in 50 ml. of dry dichloromethane; 0.9 ml. (7.6 mmoles) of triethylamine was added to the solution at $-10°$ C. Then 1.124 g. (7.6 mmoles) of phenoxyacetyl chloride in 10 ml. of dichloromethane was added dropwise and the reaction mixture was stirred for 30 minutes at $-10°$ C. The mixture was then warmed up to room temperature in another 2 hours and evaporated to dryness under reduced pressure. The residue was taken up in chloroform, washed once with a 3% sodium carbonate solution and with water and then dried over sodium sulfate. Evaporation of the solvent followed by crystallization (chloroform/petroleum ether) of the solid thus obtained gave a white crystalline material, which on recrystallization (chloroform/petroleum ether) gave 3.8 g. (72%) of cis-1-(1'-p-nitrobenzyloxycarbonyl-2'-hydroxy-propyl)-3-phenoxyacetamido-4-styryl-2-azetidinone; m.p. 130°–132° C.

IR (Nuhol): 3400, 1750, 1740, 1700 cm$^{-1}$.

NMR (CDCl$_3$): 1.45 (d, 3H) 3.9 (s, 1H), 4.45 (s, 2H ), 4.55 (2q, overlap J=not seen) 5.3 (q, s, 34 J=not seen) 6.10 (dd, 1H, J=9 Hz, J=16 Hz), 6.6→7.3 (m, 7H), 7.55 (d, 2H, J=9 Hz), 8.25, (d, 2H J=9 Hz).

CIMS: calculated: for C$_{30}$H$_{29}$N$_3$O$_8$: 559 found: 560 (M+1).

(f) To a solution of 3.0 g. (5.4 mmoles) of the product of (e) in 10 ml. of acetone were added 11 ml. of Jones reagent in dropwisemanner. The reaction mixture was stirred for another 2 hours and then evaporated to dryness. An ethyl acetate extract of the residue was washed with a 5% sodium bicarbonate solution, dried over sodium sulfate and concentrated to an oil which was chromatographed (chloroform/ethyl acetate; 10.3) to give a white solid. This product was triturated with dichloromethane to obtain 0.34 g. (20%) of cis-3-phenoxyacetamido-4-styryl-2-azetidinone as a crystalline product.

IR: 3400–3300, 1750, 1675 cm$^{-1}$.

NMR (CDCl$_3$-DMSOd$_6$): 4.40 (s, 2H), 4.40 (m, 1H, hidden), 5.35 (dd, 1M, J=5 Hz, J'=9 Hz), 6.20 (dd, 1H; J=9 Hz, J'=16 Hz), 6.60 (d, 1H, J=16 Hz) 6.70→7.4 (m, 10H), 8.1 (1H), 8.3 (d, 1H, J=9 Hz).

CIMS: calculated: for C$_{19}$H$_{18}$N$_2$O$_3$: 322. found: M+1=323.

(g) 65 mg. (0.2 mmole) of the product of (f) was placed in 5 ml of 60% aqueous acetone to which were added 6 drops of 1,4-dioxane to facilitate complete dissolution of the starting material. To the solution were then added 64 mg. (0.04 mmole) of potassium permanganate. The reaction mixture was stirred at room temperature for 2 hours and then it was filtered and evaporated; the aqueous residue was acidified with 20 ml. of 1 N HCl. The aqueous phase was extracted with ethyl acetate (2×20 ml.), the combined organic extracts were dried over sodium sulfate and evaporated to yield 55 mg. of crude cis-3-phenoxyacetamido-4-carboxy-2-azetidinone. This crude product was dissolved in 5 ml of anhydrous dichloromethane to which was added then 0.30 ml. of an ethereal solution of diazomethane. The solution was stirred at room temperature for 15 minutes and then evaporated to dryness. Chromatography of the residual oil on thick layer plates afforded 15 mg. (26.7%) of pure cis-3-phenoxyacetamido-4-methoxycarbonyl-2-azetidinone which crystallized as a white solid from dichloromethane/ether; m.p. 138°–139° C.

IR (neat): 3250–3200, 1770, 1740, 1675 cm$^{-1}$;

MNR (CDCl$_3$): 3.60 (s, 3H), 4.45 (m, 1H), 4.48(s, 2H), 5.23 (dd, 1H, J=5.0, 10.0 Hz), 6.80-7.40 (m, 7H).

EXAMPLE 16

(a) cis-1-(1'-p-nitrobenzyloxycarbonyl-2'-hydroxy-propyl)-3-phenoxyacetamido-4-styryl-2-azetidinone (prepared according to the procedures described in Example 15 (a) to (e)) was dissolved in 460 ml. of dry acetone. Then were added in dropwise fashion 8.89 ml. of Jones reagent (2.67 moles in $H_2CrO_4$) while maintaining vigorous stirring. After 2 hours the reaction mixture was filtered through a coarse scintered glass funnel and then concentrated in vacuo. The residual oil was taken up in ethyl acetate, washed with a 5% sodium bicarbonate solution (3×250 ml). and dried over sodium sulfate. The residue obtained after evaporation was crystallized from ethyl acetate/petroleum ether (b.p. 40°-60° C.) to yield 4.00 g. (44%) of cis-1-(1'-p-nitrobenzyloxycarbonyl-2'-hydroxy-propenyl)-3-phenoxyacetamido-4-styryl-2-azetidinone.

IR: 1740, 1670, 1630 $cm^{-1}$.

NMR ($CDCl_3$): 2.25 (s, 3H) 4.25 (s, 2H), 4.62 (dd, 1H, J=7 Hz, J'=9 Hz), 5.32 (dd, 1 M, hidden) 5.35 (s, 2H), 6.15 (dd, 1H, J=Hz, J'=16 Hz), 6.50 (d, 1H, J 16 Hz), 6.75→7.45 (m, 11H), 7.52 (d, 2H, J=8 Hz), 8.25 (d, 2H, J=8 Hz), NH hidden in 6.75→7.45), 13.00 (s, broad, 1).

CIMS: calculated: for $C_{30}H_{27}N_3O_8$: 557. found: M+1=558.

(b) To a solution of 1.00 g. (1.8 mmole) of the product of (a) in 25 ml. of dry dichloromethane was added 0.439 g (3.6 mmoles) of N,N-dimethylamino-pyridine in 10 ml. of dichloromethane. A solution of 0.302 g. (2.7 mmoles) of mesyl chloride in 10 ml. of dichloromethane was added at once and the reaction mixture was stirred for 5 minutes. (Thin layer chromatography of the reaction mixture after 5 minutes showed the disappearance of the starting material). The organic layer was washed with 3% HCl (3×20 ml.), once with brine and then dried over sodium sulfate. Evaporation of the solvent afforded an amorphous powder, which was redissolved in ethyl acetate/dichloromethane (1:1); the solution was filtered through silicagel (10 g.) and evaporated to obtain 0.85 g. (74.5%) of cis-1-(1'-p-nitrobenzyloxycarbonyl-2'-mesyloxy-propenyl)-3-phenoxyacetamido-4-styryl-2-azetidinone.

IR (film): 3200, 2900, 1758, 1735, 1675, 1520 $cm^{-1}$.

NMR ($CDCl_3$): 2.25 (s, 3H), 3.30 (s, 3H), 4.40 (s, 2H) 4.75 (dd, 1H, J=5 Hz), 5.25 (s, 2H), 5.45 (dd, hidden), 6.20 (dd, 2H, J=7 Hz) 6.80 (d, 1H, J=9 Hz), 6.10→7.30 (m, 11H), 7.50 (d, J=8 Hz), 8.20 (d, 2H, J=8 Hz).

A solution of ruthenium tetroxide was prepared by adding 2.5 g. of sodium periodate to a suspension of 15 mg. of ruthenium dioxide in 50 ml. of acetone/water (1:1). This solution was added to 500 mg. of the product of (b) in 10 ml. of acetone. The reaction mixture was stirred for 1 hour at room temperature, filtered and then stripped of solvent under reduced pressure. The residue was extracted with ethyl acetate and this organic solution was washed with 30 ml. of a 5% sodium bicarbonate solution. The aqueous layer was separated and then acidified with 1 N HCl and extracted with ethyl acetate. The organic phase was separated and evaporated and the residual solid was triturated with ether and filtered. There was obtained a colourless solid, which on the basis of spectral data and melting point was found to be identical with cis-3-phenoxyacetamido- 4-carboxy-2-azetidinone prepared earlier by other methods.

NMR ($CDCl_3$-$DMSOd_6$): 4.35 (d, 1H, J=5 Hz), 4.50, (s, 2H), 5.50 (dd, 1H, J=5 Hz, J=9 Hz), 6.70→7.60 (m, 6 H), 7.80 (d, 1H, J=9 Hz). 8.20 (s, 1H).

CIMS: calculated for MW: 263. found: $M^+$—$H_2O$=245.

EXAMPLE 17

To a solution of 1.18 g. (2 mmoles) of cis-1-(1'-p-nitrobenzyloxycarbonyl-2'-hydroxy-propyl)-3-phenoxyacetamido-4-styryl- 2-azetidinone (prepared according to the procedures described in Example 15 (a) to (e)) in 100 ml. of dichloromethane was added 0.832 g. (8 mmoles) of triethylamine. After the reactants had been cooled to −60° C., 0.448 g. (4 mmoles) of methanesulfonyl chloride in 10 ml.of dichloromethane was added dropwise over a period of 10 minutes. The reaction mixture was stirred for an additional hour at −60° C. and 2 hours at room temperature. Thin layer chromatography of the reaction mixture showed almost complete disappearance of the starting material. The mixture was then washed with a 0.2M dipotassium hydrogen phosphate solution (buffered at pH=4.4), with water and with brine and then dried over sodium sulfate. Evaporation of the solvent followed by chromatography on 100 g. of Davis silicagel (100–200 mesh) using chloroform/ethyl acetate (10:1) as the eluant afforded 0.765 g. (71%) of cis-1-(1'-p-nitrobenzyloxycarbonyl-propenyl)-3-phenoxyacetamido -4-styryl-2-azetidinone; m.p. 89°-90° C. after crystallization from ethyl acetate/petroleum ether.

IR (Nujol): 3300, 1750-1725, 1650 $cm^{-1}$.

NHR ($CDCl_3$): 2.1 (d, J=7.5 Hz), 4.5 (s, 2H), 5.05 (dd, 1H, J=5 Hz, J'=9 Hz), 5.3 (s, m, 3H) 6.1 (dd, 1H, J=9 Hz, J'=16), 6.65 (d, 1H, J=16 Hz), 6.75 (9, 1H, J=7.5, J'=16 Hz), 6.90→7.25 (m, 12H), 7.4 (d, 2H, J=9 Hz), 8.1 (d, 2H, J=9 Hz).

EXAMPLE 18

(a) Equimolar quantities of furfuraldehyde and p-nitrobenzyld-threonine (prepared according to the procedures described in Example 15 (a) and (b)) were refluxed together in benzene in the presence of a catalytic amount of p-toluenesulfonic acid using a Dean-Stark apparatus. After the calculated amount of water had separated, the organic solvent was evaporated under reduced pressure. There was obtained furfurylidene N-(1-p-nitrobenzyloxycarbonyl- 2-hydroxy-propyl) amine which was used for the subsequent reaction without further purification.

(b) To a suspension of 2.96 g. (14 mmoles) of potassium α-methyl-βcarbomethoxy-vinylamino-acetate in 120 ml. of anhydrous ether was added under anhydrous conditions 3.6 ml. (28 mmoles) of triethylamine at −25° C., 1.4 ml. (14 mmoles) of ethyl chloroformate was then added dropwise and the reaction mixture was stirred for 30 minutes. To this mixture was added dropwise a solution of 3.32 g. (10 mmoles) of the product of (a) in dichloromethane. The reaction mixture was stirred for an additional 30 minutes at −25° C. and for 2 hours at room temperature. Then the mixture was evaporated to dryness under reduced pressure, triturated with anhydrous ether, cooled and filtered. The solid residue was extracted with chloroform and the chloroform solution was washed with water, dried and evaporated. Column chromatography (silicagel) of the residue so obtained using chloroform/ethyl acetate (10:1) as the eluant gave 0.2 g. of cis-1-(1'-p-nitrobenzyloxycarbonyl-2'-hydroxy-propyl)-3- (α-methyl-β-carbomethoxy-vinylamino)-4-α-furyl-2-azetidinone; m.p. 147°-148° C.

IR (Nujol): 3400, 1795, 1750, 1700, 1650 $cm^{-1}$.

NMR (CDCl$_3$): 1.40 (d, 3H), 1.85 (s, 3H), 3.60 (s, 3H), 3.90 (s, 1H), 4.55 (m, 2H) 5.05 (d, 1H, J=5 Hz), 5.20 (dd, 2H, J=5 Hz, J=9 Hz), 5.32 (s, 2H), 6.50 (m, 2H), 7.52 (m, 1H) 7.55 (d, 2H, J=9 Hz), 8.25 (d, 2H, J=9 Hz), 8.90 (d, 1H, J=9 Hz).

Mass spectrum (m/e): 487.

EXAMPLE 19

A suspension of 0.01 mole of potassium α-methyl-βcarbomethoxy- vinylamino-acetate, 0.01 mole of cinnamylidene N-(1-p-nitrobenzyloxycarbonyl-2-hydroxypropyl) amine (prepared according to the procedures described in Example 15 (a) to (c)) and 0.04 mole of triethylamine in 150 ml. of dichloromethane was cooled in dry ice/CCl$_4$ bath to −20° C. under a nitrogen atmosphere. A suspension of 0.01 mole of cyanuric chloride in 50 ml. of dichloromethane was added dropwise over 15 minutes and the mixture was stirred for 1 hour at −20° C. The bath temperature was then allowed to rise to room temperature and the stirring was continued for additional 12 hours. The contents were then washed respectively, with water, an aqueous sodium bicarbonate solution and brine. The organic layer was dried over magnesium sulfate and then evaporated under reduced pressure. The residue was triturated with ethanol/ether (1:1) to afford an essentially pure sample of cis-1-(1'-nitrobenzyloxycarbonyl-2'-hydroxy-propyl)-3-(α-methyl-β-carbomethoxy-vinylamino)-4-styryl-2-azetidinone in 40% yield. Recrystallization from chloroform/ether gave an annalytically pure sample; m.p. 147°–149° C. The compound thus prepared was identical with that prepared according to the procedures of Example 15 (a) to (d).

EXAMPLE 20

Using essentially the same method as described in Example 19, cis-1-phenyl-3-(α-methyl-β-carbomethoxy-vinylamino)-4-styryl-2-azetidinone was prepared in 45% yield; m.p. 146°–148° C.

IR (Nujol): 1747 cm$^{-1}$.

NMR (CDCl$_3$): 9.08 (d, J=9 Hz, 1H), 7.56–7.0 (m, 10H), 6.84 (d, 1H) 6.2 (q, 1H), 4.9 (m, 2H), 4.56 (s, 1H), 3.53 (s, 3H), 1.90 (s, 3H).

EXAMPLE 21

3-Phenylacetamido-2-azetidinone

STEP A:

1-(2'-methyl-1'-carbomethoxy)-propenyl-3-(α-methyl-β-carbomethoxyvinylamino)-4-methylthio-2-azetidinone

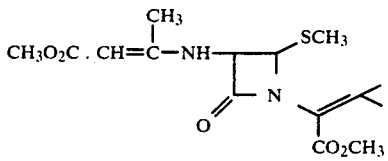

A solution of 1 mole of ethyl chloroformate in 10 ml of dichloromethane was added dropwise under anhydrous conditions to a mixture of 0.1 mole of potassium N-(1-methyl-2-methoxycarbonyl -vinyl)-aminoacetate and 0.13 mole of triethylamine in 150 ml of anhydrous ether kept at −15° to −20° C. The resulting mixture was maintained at −5° C. for 20 min. and then a solution of 0.1 mole of thioformimidate of 2-methyl-1-carbomethoxy-1-propenylamine [Bell et al, J. Org. Chem., Vol. 37 (1972), p. 2733] and 0.1 mole of triethylamine in 50 ml of dry ether and 20 of dichloromethane was dropped in with stirring over a period of one hour. The reaction mixture was stirred for 2 hrs. at 0° C. and then for 10 to 12 hr. at room temperature. The reaction mixture was then filtered and the residue on the filter was washed with dichlormethane. The combined filtrate was washed with water, dried over anhydrous magnesium sulfate and evaporated to dryness to obtain 1-(2'-methyl- 1'-carbomethoxy)-propenyl-3-(αmethyl-β-carbomethoxyvinylamino) -4-methylthio-2-azetidinone in the form of an oil.

IR Spectrum (CHCl$_3$): 1770 cm$^{-1}$ (β-lactam), 1725 cm$^{-1}$ (COOMe), 1660 (α,β-unsaturated ester) m/e M$^+$=342.

IR Spectrum (CHCl$_3$): 2.0 (S, 3H), 2.05 (S, 3H), 2.15 (S, 3H), 2.26 (S, 3H), 3.36 (S, 3H), 3.82 (S, 3H), 4.66 (S, 1H), 4.5–4.9 (m, 2H), 9.1 (d, 1H, J=9 Hz).

The resulting of vinylamino β-lactam was hydrolyzed under acidic conditions to obtain the corresponding 3-amino-β-lactam (4, ir. 1760 cm$^{-1}$, El-MS m/e 244). The structure was confirmed by an independent synthesis. Acylation of the 3-amino-β-lactam with penylacetyl chloride formed 1-(2'-methyl-1'-carbomethoxy)-propenyl-3-phenylacetamido-4-methylthio -2-azetidinone (67% yield) with a melting point of 87°–91° C. (ether).

IR Spectrum (CHCl$_3$): 1765 cm$^{-1}$ (β-lactam CO.): 1720 cm$^{-1}$ (—COOMl); 1660 cm$^{-1}$ (—NH—CO—).

NMR Spectrum: δ1.93 (S, 3H), 2.12 (S, 3H), 2.22 (S, 3H), 3.6 (S, 2H), 3.73 (S, 3H), 4.77 (q, 1H), 4.95 (d, 1H, J=2H2), 7.35 (S, 6H).

Mass Spectrum m/1 362.

STEP B:

1-(2'-methyl-1'-carbomethoxy)-propenyl-3-phenylacetamido -2-azetidinone

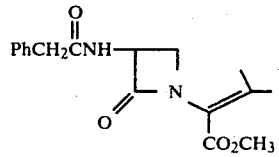

Prewashed activated Raney Nickel was added to a solution of 0.1 mole of 1-(2'-methyl-1'-carbomethoxy)-propenyl -3-phenylacetamido-4-methylthio-2-azetidinone in acetone and the mixture was refluxed. The reaction mixture was monitored by its thin layer chromatography and the reaction was completed in 20 minutes. The mixture was carefully filtered and was washed several times. The organic layer was then evaporated to obtain a 60% yield of 1-(2'-methyl-1'-carbomethoxy)-propenyl-3-phenylacetamido-2-azetidinone.

IR Spectrum (CHCl$_3$): 1759 cm$^{-1}$ (β-lactam); 1721 cm$^{-1}$ (ester). m/e+18 334.

STEP C:

1-(2'-methyl-2'-bromo-1'-hydroxy-1'-carbomethoxy)-propyl-3-phenylacetamido-2-azetidinone

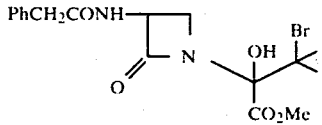

0.032 ml of 1 N sulfuric acid was added to a cooled solution (0° C.) of 0.035 g of the product of Step B dissolved in a mixture of 0.9 ml of water and 5 ml of acetone, followed by dropwise addition of a solution of N-bromosuccinimide in 0.5 ml of acetone. The reaction mixture was stirred for aprox. 1 hr. until monitoring by thin layer chromatography showed the absence of the starting compound. The mixture was then evaporated and the aqueous layer was extracted with $CHCl_3$. The organic phase was washed twice with 10% $Na_2SO_3$ to remove extra N-bromosuccinimide, was dried over anhydrous potassium carbonate and was evaporated to dryness to obtain 40 mg (87.4% yield) of 1-(2'-methyl-2'-bromo-1'-hydroxy-1'-carbomethoxy) -propyl-3-phenylacetamido-2-azetidinone.

CIMS ($CF_2Cl_2$) 447 and 449 (1:1).

IR Spectrum )$CHCl_3$): 1755 $cm^{-1}$ (β-lactam CO.) 1725 $cm^{-1}$ (—COOMe).

STEP D: 3-Phenylacetamido-2-azetidinone 40 mg of the product of Step C were dissolved in 5 ml of $CH_2Cl_2$ and the excess triethylamine was added thereto. The mixture was stirred overnight at room temperature and the solvent was then removed under reduced pressure. Excess triethylamine was aezotropically removed (benzene, 2×50 ml) and the resulting oil was taken up in 20 ml of chloroform. The solution was washed with 20 ml of sodium chloride solution, dried over potassium carbonate and evaporated to dryness to 15 mg (76.4% yield) of 3-phenylacetamido-2-azetidinone in the form of an oil.

IR Spectrum $CHCl_3$): 1760 $cm^{-1}$ (β-lactam CO).

NMR Spectrum: 3.5 (S, 2H), 3.6 (m, 2H), 5.0 (m, 1H), 6.9 (m, 1H), 7.3 (S, 6H).

CIMS ($NH_3$)=222. $M^+ + 18$.

The said compound and related azetidinone derivatives are disclosed by Fujisawa Pharmaceutical Company to be useful as antimicrobial agents.

Various modifications of the products and processes of the invention may be made without departing from the spirit or scope thereof and it is to be understood that the invention is intended to be limited only as defined in the appended claims.

We claim:

1. Process for the preparation of β-lactams of the formulae:

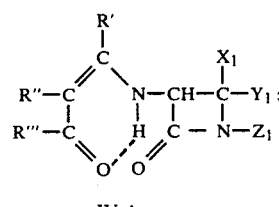

IV A

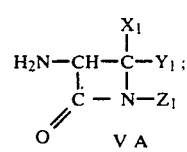

V A

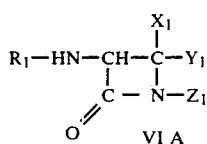

VI A wherein R' is selected from the group consisting of lower alkyl, aryl and aryl(lower alkyl), R" is selected from the group consisting of hydrogen and lower alkyl or R' and R" together with the carbon atoms to which they are attached are lower cycloalkyl and R'" is selected from the group consisting of lower alkyl and —OR, wherein R is lower alkyl, $Y_1$ is selected from the group consisting of hydrgen, furyl, phenyl, optionally substituted by methoxy or dimethylamino, styryl, optionally esterified carboxy and hydroxymethylene, $X_1$ is slected from the group consisting of hydrogen and methylthio or $X_1$ together with $Y_1$ is 1,5-pentylene, $Z_1$ is selected from the group consisting of hydrogen, methyl optionally substituted by phenyl and phenyl optionally substituted with at least one member of the group consisting of halogen, methyl, methoxy, methylthio and dimethylamino, or $Z_1$ is

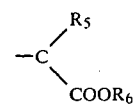

wherein $R_5$ is selected from the group, consisting of ethyl and ethylidene optionally substituted by optionally esterified hydroxy, $R_6$ is selected from the group consisting of hydrogen and carboxylic ester groups and $R_1$ is an acyl of an organic carboxylic acid of 1 to 8 carbon atoms, comprising reacting an 1,3-dicarbonyl compound of the formula:

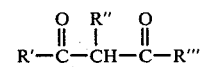

I A with glycine in the presence of a base MOH, wherein M is an alkali metal to form a vinylamino salt of the formula:

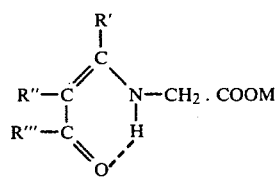

II A activating the carboxyl group of the compound obtained with an activating agent selected from the group consisting of lower alkyl haloformate esters, di(lower alkyl) and diaryl phosphochloridates and cyanuric chloride, and reacting the activated compound in the presence of a tertiary base with an imino of the formula:

III A to form the corresponding α-vinylamino-β-lactam of formula IV A and if desired, subjecting the compound thus obtained to mild acid hydrolysis to form the corresponding α-amino-βlactam of formula V A.

2. The process of claim 1 wherein the compound of formula V A is reacted with a carboxylic acylating agent to obtain a compound of formula VI A.

3. The process of claim 1 wherein R' is selected from the group consisting of methyl and phenyl, R" is hydrogen or R' and R" together with the carbon atoms to which they are attached are cyclopentyl or cyclohexyl and R''' is selected from the group consisting of methyl, methoxy, ethoxy and t.butoxy.

4. The process of claim 1 wherein R' is methyl, R'' is hydrogen and R''' is selected from the group consisting of methoxy and ethoxy.

5. The process of claim 1 wherein the base MOH is potassium hydroxide.

6. The process of claim 1 wherein the activating agent is selected from the group consisting of methyl, ethyl and t.butyl chloroformate diethyl and diphenyl phosphocloridate an cyanuric chloride.

7. The process of claim 1 wherein the activating agent is selected from the group consisting of methyl and ethyl chloroformate and cyanuric chloride.

8. The process of claim 1 wherein the tertiary base is triethylamine.

9. An α-vinylamino-β-lactam of the formula:

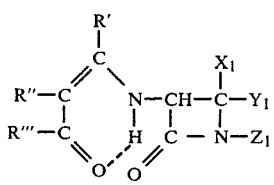

IV A wherein R' represents lower alkyl or phenyl, R''represents hydrogen or lower alkyl or R' and R'' togeher with the carbon atoms to which they are attached represent lower cycloalkyl, R''' represents lower alkyl or a group —OR, wherein R represents lower alkyl, $Y_1$ is selected from the group consisting of hydrogen, furyl, phenyl optionally substituted by methoxy or dimethyl-amino, styryl, optionally esterified carboxyl and hydroxymethylene, $X_1$ is selected from the group consisting of hydrogen and methylthio or $X_1$ together with $Y_1$ is 1,5-pentylene, $Z_1$ is selected from the group consisting of hydrogen methyl optionally substituted by phenyl and phenyl optionally substituted with at least one member of the group consisting of halogen, methyl, methoxy, methylthio and dimethylamino, or $Z_1$ is

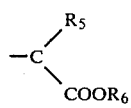

wherein $R_5$ is selected from the group consisting of ethyl and ethylidene optionally substituted by optionally esterified hydroxy and $R_6$ is selected from the group consisting of hydrogen and carboxylic ester groups.

10. The α-vinylamino-βlactam according to claim 9, 1-vertatyl-3-(α-methyl-β-carbomethoxy-vinylamino)-4-(β-styryl)-2-azetidinone.

11. The α-vinylamino-β-lactam according to claim 9, 1-veratryl-4-furyl-3-(α-methyl-β-carbomethoxy-vinylamino)-2-azetidinone.

12. The α-vinylamino-βlactam according to claim 9, cis-1(1'-p-nitrobenzyloxycarbonyl-2'-hydroxy-propyl)-3-(αmethyl-β-carbomethoxy-vinylamino) -4-styryl-2-azetidinone.

13. The α-vinylamino-β-lactam according to claim 9, cis-1-(1'-p-nitrobenzyloxycarbonyl-2'-hydroxy-propyl)-3-(αmethyl-βcarbomethoxy-vinylamino)-4-α-furyl-2-azetidinone.

14. The α-vinylamino-βlactam according to claim 9, cis-1-phenyl-3-(α-methyl-β-carbomethoxy-vinylamino)-4-styryl-2-azetidinone.

15. An α-amino-β-lactam of the formula:

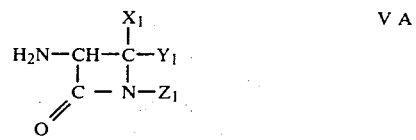

V A wherein $Y_1$ is selected from the group consisting of hydrogen, furyl, phenyl optionally substituted by methoxy or dimethyl-amino, styryl, optionally esterified carboxy and hydroxymethylene, $X_1$ is selected from the group consisting of hydrogen and methylthio or $X_1$ together with $Y_1$ is 1,5-pentylene, $Z_1$ is

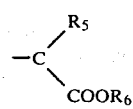

wherein $R_5$ is selected from the group consisting of ethyl and ethylidene optionally substituted by optionally esterified hydroxy, $R_6$ is selected from the group consisting of hydrogen and carboxylic ester groups.

16. The α-amino-β-lactam according to claim 15, cis-3-amino-1-(1'-p-nitrobenzyloxycarbonyl-2'-hydroxy-propyl)-4-styryl-2-azetidinone.

17. An α-acylamido-β-lactam of the formula:

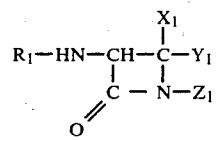

VI A wherein $Y_1$ is selected from the group consisting of hydrogen, furyl, phenyl, optionally substituted by methoxy or dimethyl-amino, styryl, optionally esterified carboxy and hydroxymethylene, $X_1$ is selected from the group consisting of hydrogen and methylthio or $X_1$ together with $Y_1$ is 1,5-pentylene, $Z_1$ is

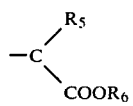

wherein $R_5$ is selected from the group consisting of ethyl and ethylidene optionally substituted by optionally esterified hydroxy, $R_6$ is selected from the group consisting of hydrogen and carboxylic ester groups and $R_1$ is an acyl of a organic carboxylic acid of 1 to 18 carbon atoms.

18. The α-acylamido-β-lactam according to claim 17, cis-1-(1'-p-nitrobenzyloxycarbonyl-2'-hydroxy-propyl)-3-phenoxyacetamido-4-carboxy-2-acetidinone.

19. The α-acylamido-β-lactam according to claim 17, cis-1-(1'-p-nitrobenzyloxycarbonyl-2'-hydroxy-propenyl)-3-phenoxyacetamido-4-styryl-2-azetidinone.

20. The α-acylamido-β-lactam according to claim 17, cis-1-(1'-p-nitrobenzyloxycarbonyl-2'-mesyloxy-propenyl)-3-phenoxy-acetamido-4-styryl-2-azetidinone.

21. The α-acylamido-β-lactam according to claim 17, cis-1-(1'-p-nitrobenzyloxycarbonyl-propenyl)-3-phenoxy-acetamido-4-styryl-2-azetidinone.

22. An α-acylamido-β-lactam of the formula:

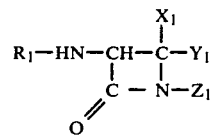

VI A wherein $X_1$ and $Z_1$ are hydrogen, $Y_1$ is selected from the group consisting of styryl and carboxyl and $R_1$ is an acyl of an organic carboxylic acid of 1 to 18 carbon atoms.

23. The α-acylamido-β-lactam according to claim 22, cis-3-phenoxy-acetamido-4-styryl-2-azetidinone.

24. The α-acylamido-β-lactam according to claim 22, cis-3-phenoxy-acetamido-4-styryl-2-azetidinone.

* * * * *

UNITED STATES PATENT AND TRADEMARK OFFICE
CERTIFICATE OF CORRECTION

PATENT NO. : 4,260,743
DATED : April 7, 1981
INVENTOR(S) : Ajay K. Bose

It is certified that error appears in the above—identified patent and that said Letters Patent is hereby corrected as shown below:

Column 5, line 42: "pripionic" should read -- propionic --.

Column 8, line 28: "4tosyloxymethyl" should read -- 4-tosyloxymethyl --.

Column 9, line 12: "62-lactam" should read -- β-lactam --.

line 22: "α-carbomethoxy" should read -- β-carbomethoxy --.

Column 12: line 22: "4phenyl" should read -- 4-phenyl --.

Column 13, line 17: "β-methyl-βcarbomethoxy" should read -- α-methyl-β-carbomethoxy --.

line 34: "740" should read -- 1740 --.

Column 14, line 15: Before "6.05" please insert
-- 4.6 (d, 2H, J = 5Hz), 4.9 (dd, 1H J = 4.5 Hz, J' = 9 Hz), --.

line 51: "1 HCl" should read -- 1N HCl --.

Column 15, line 60: "(62 styryl)" should read -- (β-styryl) --.

Column 16, line 36: "MNR" should read -- NMR --.

line 63: "M" should read "m".

UNITED STATES PATENT AND TRADEMARK OFFICE
CERTIFICATE OF CORRECTION

PATENT NO. : 4,260,743

DATED : April 7, 1981

INVENTOR(S) : Ajay K. Bose

It is certified that error appears in the above—identified patent and that said Letters Patent is hereby corrected as shown below:

Column 19, line 41: "methy" should read -- methyl --.

line 63: "(8.6 mmoles)" should read -- (7.6 mmoles) --.

Column 20, line 67: "MNR" should read -- NMR --.

Column 22, line 1: "H-" should read -- $H_2O$ --.

line 2: Delete "$_2O$".

line 37: "nitrobenzyld-" should read -- nitrobenzyl-d- --.

line 48: "βcarbomethoxy-" should read -- β-carbomethoxy- --.

Column 24, line 9; Column 27, lines 62 and 67: "(αmethyl" should read -- (α-methyl --.

lines 35 and 54: "1-(2'-methyl-1'-" should read -- 1-(2-methyl-1- --.

Column 25, line 17: ")$CHCl_3$)" should read -- ($CHCl_3$) --.

Column 26, line 6: "hydrgen" should read -- hydrogen --.

lines 26-27: "1 to 8 carbon atoms" should read -- 1 to 18 carbon atoms --.

Column 26, line 61; Column 27, lines 54 and 60: "βlactam" should read -- β-lactam --.

UNITED STATES PATENT AND TRADEMARK OFFICE
CERTIFICATE OF CORRECTION

PATENT NO. : 4,260,743
DATED : April 7, 1981
INVENTOR(S) : Ajay K. Bose

It is certified that error appears in the above—identified patent and that said Letters Patent is hereby corrected as shown below:

Column 27, line 55: "vertatyl" should read -- veratryl --.

Column 28, line 1, "βlactam" should read -- β-lactam --.

Column 28, line 3 of Claim 18: delete "carboxy" and insert -- styryl --.

Column 30, line 2 of Claim 23: delete "styryl" and insert -- carboxy --.

Signed and Sealed this

Fifth Day of January 1982

[SEAL]

Attest:

GERALD J. MOSSINGHOFF

*Attesting Officer*   *Commissioner of Patents and Trademarks*